United States Patent [19]

Nadelson

[11] 4,086,243
[45] Apr. 25, 1978

[54] INTERMEDIATES IN THE PREPARATION OF ISOXAZOLYL BENZAMIDES

[75] Inventor: Jeffrey Nadelson, Lake Parsippany, N.J.

[73] Assignee: Sandoz, Inc., E. Hanover, N.J.

[21] Appl. No.: 707,681

[22] Filed: Jul. 22, 1976

Related U.S. Application Data

[62] Division of Ser. No. 549,934, Feb. 14, 1975, Pat. No. 3,987,179.

[51] Int. Cl.$^2$ .................. C07D 209/36; C07D 209/48
[52] U.S. Cl. ............................................. 260/325 PH
[58] Field of Search ..................... 260/325 PH, 325 R

[56] References Cited

FOREIGN PATENT DOCUMENTS 974,894  11/1964  United Kingdom ............ 260/325 R

*Primary Examiner*—Ethel G. Love
*Attorney, Agent, or Firm*—Gerald D. Sharkin; Robert S. Honor; Timothy G. Rothwell

[57] ABSTRACT

Substituted or unsubstituted isoxazolyl benzamides, e.g., o-(3-phenylisoxazol-5-yl)-N-methylbenzamide, are prepared by cyclizing a corresponding 1-hydroxy-1-[substituted or unsubstituted -β-(hydroxyimino)phenethyl]-2-alkyl phthalimidine with a strong acid and are useful as minor tranquilizers, muscle relaxants, and sleep inducers.

1 Claim, No Drawings

INTERMEDIATES IN THE PREPARATION OF ISOXAZOLYL BENZAMIDES

This is a division of application Ser. No. 549,934, filed Feb. 14, 1975, now U.S. Pat. No. 3,987,179.

This invention relates to isoxazolyl benzamides which exhibit minor tranquilizer, muscle relaxant and sleep inducer activity. More particularly, it relates to substituted or unsubstituted isoxazolyl benzamides, intermediates thereof, and to processes for their preparation.

The compounds of this invention may be represented by the following structural formula:

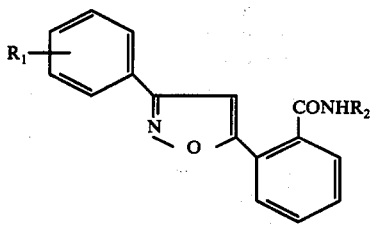
(I)

where
$R_1$ represents hydrogen, halo having an atomic weight of about 19 to 36, i.e., fluoro or chloro, straight chain lower alkyl, i.e., straight chain alkyl having 1 to 4 carbon atoms, e.g., methyl, ethyl, propyl and the like, straight chain lower alkoxy, i.e., straight chain alkoxy having 1 to 4 carbon atoms, e.g., methoxy, ethoxy, propoxy and the like, or trifluoromethyl, and
$R_2$ represents straight chain lower alkyl as defined above.

The compounds of formula (I) are prepared according to the following reaction scheme:

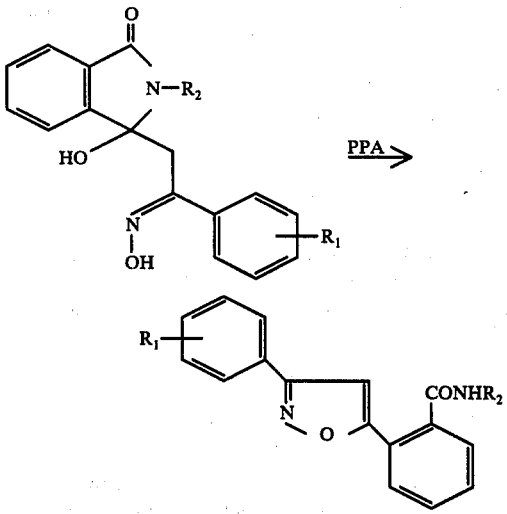

where $R_1$ and $R_2$ are as defined above.

The compounds of formula (I) are prepared by cyclizing a compound of the formula (II) with a polyphosphoric acid. Although inert solvents such as diethyl ether, tetrahydrofuran, dioxane, aliphatic hydrocarbons, aromatic hydrocarbons, or halogenated hydrocarbons can be used, it is preferred that the reaction be carried out in excess of the polyphosphoric acid. The temperature of the reaction is not critical, but it is preferred that the reaction be carried out at a temperature between about 80° to 150° C., preferably from about 100° to 110° C. The reaction may be run from 1 to 6 hours, preferably from about 2 to 4 hours. The product is recovered by conventional techniques, e.g., evaporation and crystallization.

The compounds of formula (II) are prepared according to the following reaction scheme:

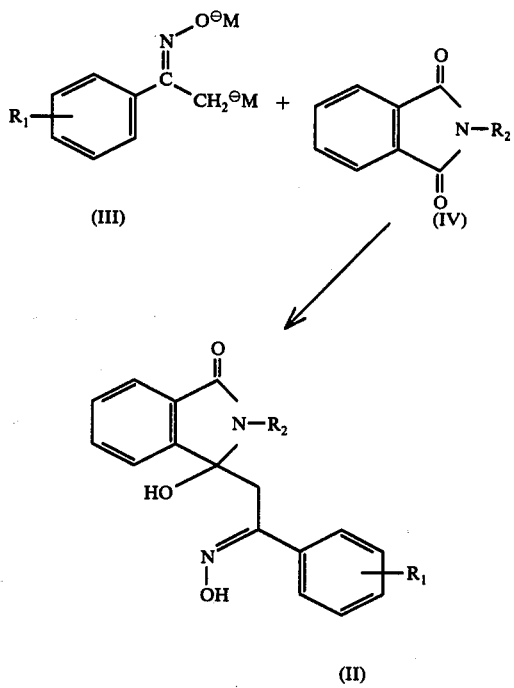

where M is an alkali metal, e.g., sodium potassium or lithium, and $R_1$ and $R_2$ are as defined above.

The compounds of formula (II) are prepared by reacting a compound of formula (III) with a compound of formula (IV) in an inert solvent. The particular inert solvent used is not critical, but it is preferred that the reaction be carried out in the presence of the ethers, such as tetrahydrofuran, dioxane, diethyl ether and the like or the aliphatic hydrocarbons such as heptane, hexane and the like, preferably tetrahydrofuran. The temperature of the reaction is not critical, but it is preferred that the reaction be carried out at a temperature between about 0° to 80° C., preferably at room temperature. The reaction may be run from 1 to 12 hours, preferably from about 1½ to 3 hours. The resulting adduct of the compounds of formulae (III) and (IV) is hydrolyzed to the compounds of formula (II) using conventional techniques, e.g., by use of ammonium chloride solution. The product is recovered using conventional techniques, e.g., evaporation and recrystallization.

It is to be noted that the compounds of formula (II) also exist in the following tautomeric forms and said tautomeric forms are also included within this invention.

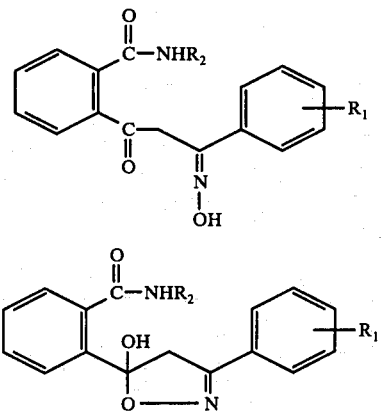

(IIa)

(IIb)

Many of the compounds of formulae (III) and (IV) are known and may be prepared by methods described in the literature. The compounds of formulae (III) and (IV) not specifically disclosed may be prepared by analogous methods from known starting materials.

The compounds of formula (I) are useful because they possess pharmacological activity. In particular, the compounds are useful as central nervous system depressants, especially as sleep inducers, minor tranquilizers, and muscle relaxants as indicated by (1) their ability to produce docility in behavior tests in mice given 25 to 200 mg/kg of animal body weight, i.p. of the test compound according to the 30-word adjective check sheet system basically as described by Irwin S. Gordon (Research Conference, Medicinal Chemistry, 1959) and Chen (Symposium on Sedative and Hypnotic Drugs, Williams and Wilkins, 1954); (2) by their ability to antagonize chronic convulsions and death in mice given 33 to 125 mg/kg i.p. of the test compound followed by 50 mg/kg i.p. of N-sulfamoylazepine; (3) by the hexobarbital reinduction method of Winter, (J. Pharmacol and Exp. Therap., 94, 7–11, 1948) in which the reinduction of anesthesia after recovery from hexobarbital induced anesthesia is used to determine sedative-hypnotic activity in mice given 70 mg/kg of animal body weight, i.p. of hexobarbital followed immediately after the mice regain their righting reflexes by 25 to 200 mg/kg of animal body weight, i.p. of the test compound; (4) as indicated in Cebus monkey using chlonically implanted electrodes. Brain readings are obtained via a ten or sixteen channel electroencephalograph. For the recording sessions, the monkeys are restrained by neck and waist plates in chairs in full side observation cages at the same time every night for 13½ hours Monday through Thursday. Gross behavior is monitored via closed circuit television and video tape recordings. The compounds of formula (I) are administered p.o. at a dosage of from about 1.8 to about 30 mg/kg immediately on placing the monkey in the observation cages with at least seven days intervening between drug administration. Physiological saline is administered via a similar route and at the same time on all control runs. Control data are collected at least 3 days per week and accumulated to give control date for 15 sessions per monkey. Data from each session are statistically compared via computer analysis to the previous 5–15 control sessions for the particular animal, with particular emphasis given to the following phases of the sleep-wakefulness cycle: resting awake, light sleep, deep sleep, paradoxical (REM) sleep, "pseudo-"paradoxical sleep, latency to onset of deep sleep, and latency to onset of first epoch of paradoxical sleep; (5) as indicated in the cat given typically 5 to 30 mg/kg of animal body weight of the active material and tested in sleep studies using chronic cortical and subcortical electrode placements, with eye movement measured via electro-oculogram. Brain readings are obtained via Gross Model 6 electroencephalograph, and the gross behavior of the animal is monitored via closed circuit television and video tape recordings; and (6) by scoring for loss of righting reflex according to the method of Reed-Muench (American Journal of Hygiene, 27:493–497, 1938) in which mice are administered 12.5 L mg/kg i.p. thioridazine, immediately after which test compound is administered at dosages of 5 to 100 mg/kg in a volumne of 0.1 ml/10 g. body weight. Thirty minutes after dosing, the mice are scored for loss of righting reflex.

For such usage, the compounds may be administered orally or parenterally as such or admixed with conventional pharmaceutical carriers.

The dosage of active ingredient employed for minor tranquilizer and muscle relaxant use may vary depending on the severity of the condition being treated. However, in general, satisfactory results are obtained when a compound of formula (I) is administered at a daily dosage of from about 1 milligram to about 200 milligrams per kilogram of animal body weight p.o., preferably given in divided doses 2 to 4 times a day, or in sustained release form. For most larger mammals (e.g., primates), the total daily dosage is from about 60 milligrams to about 1500 milligrams. Dosage forms suitable for internal use comprise from about 15 to about 750 milligrams of active compound in intimate admixture with a solid or liquid pharmaceutically acceptable carrier or diluent.

The dosage of active ingredient employed for sleep inducer use may vary depending on the severity of the condition being treated. However, in general, satisfactory results are obtained when a compound of the formula (I) is administered at a daily dosage of from about 2 milligrams to about 150 milligrams per kilogram of animal body weight p.o., typically given in a single dose at bedtime. For most larger mammals, the total daily dosage is from about 150 milligrams to about 1500 milligrams, preferably at bedtime in a single dose, and dosage forms suitable for internal administration comprise from about 35 to about 750 milligrams of the compound in admixture with a solid or liquid pharmaceutical carrier or diluent. The preferred pharmaceutical compositions from the standpoint of preparation and ease of administration are solid compositions, particularly hardfilled capsules and tablets.

EXAMPLE 1

1-Hydroxy-1-[β-(hydroxyimino)phenethyl]-2-methylphthalimidine

A solution of 5.4 g. (0.04 mole) acetophenone oxime in 90 ml. tetrahydrofuran is cooled to 0° C and there is added dropwise 55 ml. n-butyllithium in hexane (0.088 mole) with the temperature not exceeding +5° C during the addition. After the addition is complete, the mixture is stirred for 2½ hours at 0° C and then warmed to room temperature, and there is added dropwise a solution of 7.08 g. (0.044 mole) N-methyl phthalimide in 85 ml. tetrahydrofuran. After the addition is complete, the mixture is stirred for 1½ hours at room temperature, then cooled to 0° C and quenched by the addition of saturated ammonium chloride. The layers are separated and the organic phase is washed with ammonium chloride solution, dried and evaporated in vacuo. The solid residue is triturated with ether, filtered and recrystallized from ethyl acetate to give 1-hydroxy-1-[β-(hydroxyimino)phenethyl]-2-methylphthalimidine, m.p. 142.5°–143.5° C.

Following the above procedure and using in place of acetophenone oxime an equivalent amount of (a) p-chloroacetophenone oxime,
(b) p-methylacetophenone oxime,
(c) p-methoxyacetophenone oxime, or
(d) m-trifluoromethylacetophenone oxime, there is obtained (a) 1-hydroxy-1-[4-chloro-β-(hydroxyimino)phenethyl]-2-methylphthalimidine,
(b) 1-hydroxy-1-[4-methyl-β-(hydroxyimino)phenethyl]-2-methylphthalimidine,
(c) 1-hydroxy-1-[4-methoxy-β-(hydroxyimino)phenethyl]-2-methylphthalimidine, or
(d) 1-hydroxy-1-[3-trifluoromethyl-β-(hydroxyimino)phenethyl]-2-methylphthalimidine, respectively.

EXAMPLE 2 o-(3-phenylisoxazol-5-yl)-N-methyl benzamide

A mixture of 55 g. (0.186 mole) 1-hydroxy-1-[β-(hydroxyimino)phenethyl]-2-methylphthalimidine and 550 grams of polyphosphoric acid is heated at 100° C. for 2 hrs. The mixture is poured onto ice and extracted with methylene cloride. The methylene chloride is washed with brine, dried over magnesium sulfate and evaporated in vacuo. The residue is crystallized from ether/methylene chloride and recrystallized from benzene to give o-(3-phenylisoxazol-5-yl)-N-methyl benzamide, m.p. 119°–121° C.

Following the above procedure and using in place of 1-hydroxy-1-[β-(hydroxyimino)phenethyl]-2-methylphthalimidine, an equivalent amount of (a) 1-hydroxy-1-[p-chloro-β-(hydroxyimino)phenethyl]-2-methylphthalimidine,
(b) 1-hydroxy-1-[p-methyl-β-(hydroxyimino)phenethyl]-2-methylphthalimidine,
(c) 1-hydroxy-1-[p-methoxy-β-(hydroxyimino)phenethyl]-2-methylphthalimidine, or
(d) 1-hydroxy-1-[m-trifluoromethyl-β-(hydroxyimino)phenethyl-2-methylphthalimidine, there is obtained (a) o-(3-p-chlorophenylisoxazol-5-yl)-N-methyl benzamide,
(b) o-(3-p-tolylisoxazol-5-yl)-N-methyl benzamide,
(c) o-(3-p-methoxyphenylisoxazol-5-yl)-N-methyl benzamide, or
(d) o-(3-m-trifluoromethylphenylisoxazol-5-yl)-N-methyl benzamide, respectively.

The o-(3-phenylisoxazol-5-yl)-N-methyl benzamide of this example is an effective sleep inducer when orally administered to an animal in need of said treatment at a dosage of 200 mg. just before bedtime. The o-(3-phenylisoxazol-5-yl)-N-methyl benzamide of this example is also an effective minor tranquilizer and muscle relaxant when orally administered to an animal in need of said treatment at a dosage of 100 mg. 2 to 4 times per day.

What is claimed is:
1. A compound of the formula

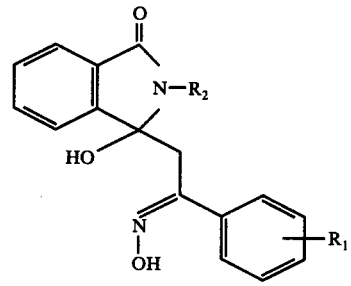

where
R$_1$ represents hydrogen, halo having an atomic weight of about 19 to 36, straight chain lower alkyl having 1 to 4 carbon atoms, straight chain lower alkoxy having 1 to 4 carbon atoms, or trifluoromethyl, and
R$_2$ represents straight chain lower alkyl.

* * * * *